United States Patent [19]

Clark et al.

[11] 4,182,575
[45] Jan. 8, 1980

[54] APPARATUS FOR INSPECTING FLAT GLASS

[75] Inventors: Donald G. Clark, Whitby; Anthony Preston, Don Mills, both of Canada

[73] Assignee: Pilkington Glass Industries Limited, Scarborough, Canada

[21] Appl. No.: 906,801

[22] Filed: May 17, 1978

[30] Foreign Application Priority Data

May 26, 1977 [CA] Canada .................................. 279202

[51] Int. Cl.² .......................................... G01N 21/16
[52] U.S. Cl. .................................... 356/430; 356/239
[58] Field of Search ................ 356/237, 239, 430, 431

[56] References Cited

U.S. PATENT DOCUMENTS

| 2,247,047 | 6/1941 | Bishop, Jr. ............................ 356/239 |
| 3,304,834 | 2/1967 | Ollfisch et al. ....................... 356/239 |
| 3,759,620 | 9/1973 | Cushing et al. ...................... 356/430 |
| 3,871,773 | 3/1975 | Shaw, Jr. .............................. 356/239 |
| 3,925,049 | 12/1975 | Schwenninger ..................... 356/239 |

Primary Examiner—Vincent P. McGraw
Attorney, Agent, or Firm—Sughrue, Rothwell, Mion, Zinn and Macpeak

[57] ABSTRACT

The invention provides novel apparatus for detecting and marking defects in flat glass advancing on a conveyor, for example a ribbon of float glass. There are two viewing stations on opposite sides of the center of the conveyor and spaced longitudinally so that there is staggered viewing of the two halves of the width of the advancing glass. Light reflected obliquely through each half is received on a viewing screen mounted above the respective side of the conveyor. Images of defects are recognized by examiners or cameras viewing the screens and the defects are marked by operation of appropriate marker guns positioned above the conveyor.

6 Claims, 2 Drawing Figures

APPARATUS FOR INSPECTING FLAT GLASS

BACKGROUND OF THE INVENTION

1. Field of the Invention

This invention relates to apparatus for inspecting flat glass for defects. More especially the invention relates to apparatus for the continuous inspection of a moving ribbon of flat glass for example a ribbon of annealed float glass which is approaching a cutting station.

2. Description of the Prior Art

The continuous inspection of the moving ribbon of flat glass travelling on a roller conveyor has been proposed by employing apparatus which includes a light source which projects light at an angle through the whole width of the ribbon of glass. The light source is positioned above the ribbon and the light transmitted through the glass is received on a screen which is positioned beneath the ribbon and is substantially horizontal.

To ensure continuous illumination of the screen there is a gap in the roller conveyor equivalent to two of the conveyor rollers. The screen is positioned beneath this gap and receives the light transmitted through the glass. Also an examiner seated above the conveyor just downstream of that gap has an uninterrupted view through the ribbon of the screen on which images of defects in the ribbon of glass appear as shadows.

Thus defects which cast shadows on the screen are monitored visually by the examiner who marks the ribbon where the defect exists using an ink marker on the end of a pointer. The sensitivity of detection of defects of different sizes is adjusted by raising or lowering the screen relative to the glass in the gap in the conveyor.

This inspection apparatus has the disadvantage that at high ribbon speeds the examiner has only a very short time, for example 2 to 3 seconds, to identify, locate and mark a defect. A significant level of unmarked defects remain in the glass. This makes necessary further visual examination of the glass after it had been cut into sheets at the cutting station. This is a particular problem when glass of high quality is required.

It is not usually practicable to reduce ribbon speed in order to increase viewing time when there are high production demands since this would give rise to an increase in production costs.

Viewing time might be increased by removing more than two rollers from the conveyor to provide the viewing zone and thereby increase the length of the ribbon under examination. This is hazardous however since the length of the unsupported ribbon is increased which can lead to breakages in the ribbon with disruption of production.

In this prior method the maximum sensitivity available by lowering the screen is limited for example to a magnification factor of about 1.4. Generally the magnification is non-linear across the width of the screen.

It is a main object of the present invention to provide an improved inspection apparatus and to improve the working conditions for examiners.

SUMMARY OF THE INVENTION

The invention provides apparatus for inspecting flat glass for defects, including a conveyor for the glass and two viewing stations disposed one on each side of the centre line of the conveyor and spaced relative to each other along the conveyor. At each viewing station a light source and a reflector are positioned to reflect light from the source obliquely through flat glass on the conveyor. A viewing screen is positioned at each viewing station to receive that light after its passage through the glass.

Preferably the conveyor is a roller conveyor and the conveyor rollers extend over part only of the conveyor width at each viewing station to provide an uninterrupted viewing area at each viewing station.

Thus about one half of the width of the glass is always supported so that the viewing area at each viewing station can be longer than the space occupied by two conveyor rollers, for example the viewing area can be equivalent to the space occupied by four conveyor rollers.

The conveyor rollers may end just short of the centre line of the conveyor alongside each viewing station so that each viewing area extends over the centre line of the conveyor. This facilitates detection of defects in the part of the glass supported by the central part of the conveyor. It is in this region that the two viewing areas overlap.

At each viewing station the viewing screen is preferably located in an upright position above the conveyor. The light source and reflector at each viewing station are positioned below the conveyor to reflect light obliquely through the glass on the conveyor at an acute angle to the plane of the conveyor. An image of a defect in the glass thus first appears at the top of the screen and moves down the screen at a progressively slower speed as the defect moves towards the bottom of the screen.

Each viewing screen may be a rear-projection screen which is located in an upright position above the conveyor. Light transmitted obliquely through the glass is incident on the front face of the screen. Preferably a platform for an examiner may be positioned over the conveyor behind the screen so that the examiner can view the rear face of the screen.

A bank of marker guns is positioned above the conveyor at each viewing station. The examiner has an operating console connected to the marker guns so that he can cause the appropriate marker gun to mark the glass in the vicinity of any defect which the examiner recognises by its image on the screen.

BRIEF DESCRIPTION OF THE DRAWINGS

An embodiment of the invention will now be described, by way of example, with reference to the accompanying drawings in which.

DESCRIPTION OF THE PREFERRED EMBODIMENTS

Figure 1:
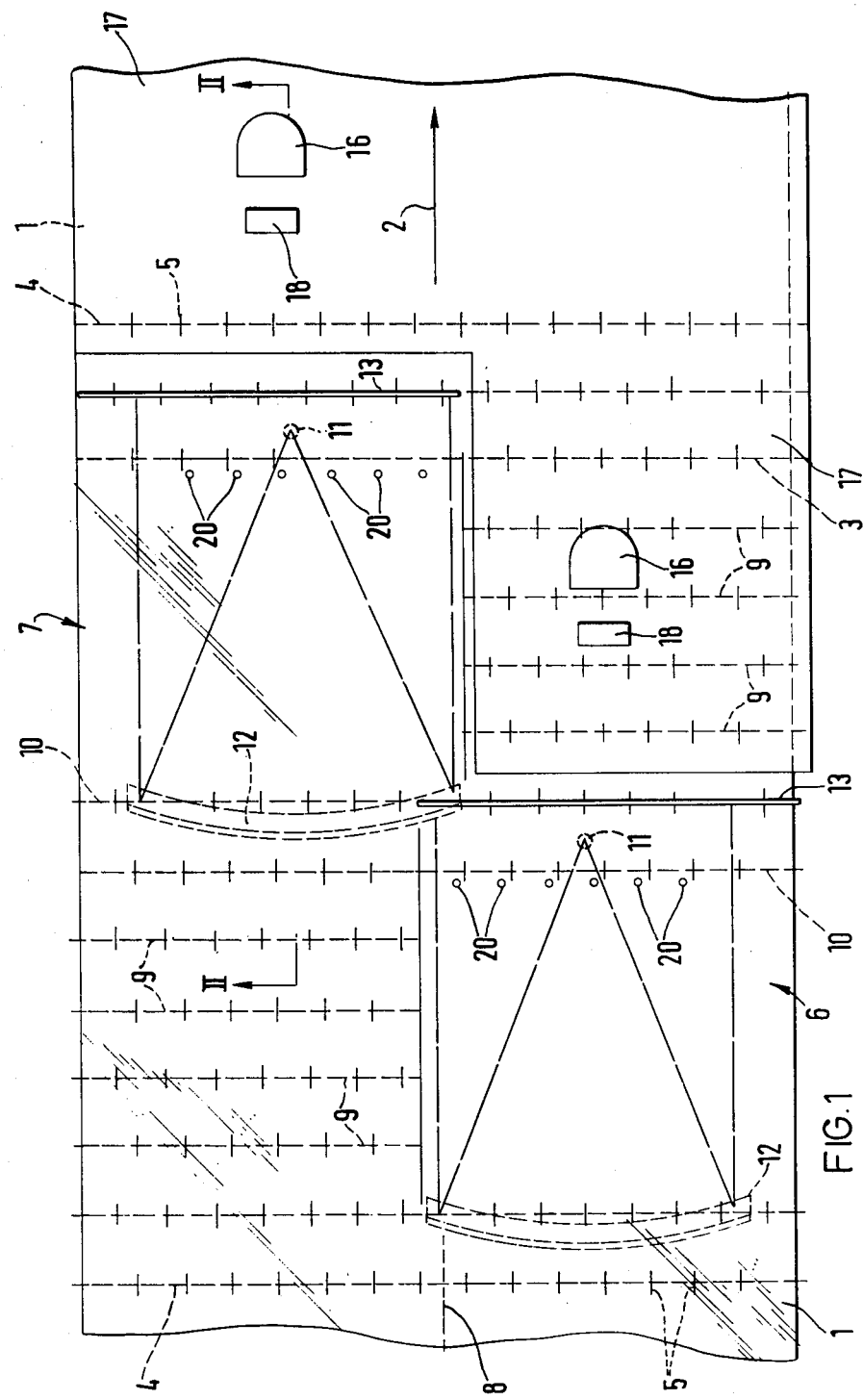
FIG. 1 is a diagrammatic plan view of a conveyor with apparatus according to the invention for inspecting flat glass advancing on the conveyor.

In FIG. 1 a ribbon of flat glass 1 is moving in the direction of arrow 2 from left to right and is supported on a roller conveyor comprising spaced rollers indicated generally at 3. Each roller is of conventional kind comprising a shaft 4 mounted in end bearings and conveyor rings 5 spaced apart on the roller for supporting the ribbon of glass.

For inspecting the ribbon of flat glass 1 for defects there are two viewing stations indicated generally at 6 and 7 disposed one on each side of the centre line 8 of the conveyor and spaced relative to each other along the conveyor. Alongside the viewing station 6 the conveyor rollers extend over part only of the conveyor width and end just short of the centre line 8 of the conveyor alongside the viewing station. These short conveyor rollers are indicated at 9 and there are four of these short conveyor rollers so that at the viewing station 6 there is an uninterrupted viewing area whose length in the direction of advance of the glass on the conveyor corresponds to the space occupied by four conveyor rollers.

Between the two viewing areas there are two full width conveyor rollers indicated at 10. The viewing area 7 at the other side of the conveyor width has a similar uninterrupted viewing area of length equivalent to the space occupied by four conveyor rollers, there being four short conveyor rollers 9 alongside the viewing station 7.

Because the short rollers 9 alongside each viewing station end just short of the centre line 8 of the conveyor each uninterrupted viewing area extends over the centre line of the conveyor. This facilitates detection of defects in the part of the glass supported by the central part of the conveyor.

In the embodiment illustrated the viewing area at each viewing station had an unobstructed length of 1.75 m. While one half of the glass ribbon is unsupported at the viewing station 6 the other half of the ribbon is supported by the short rollers 9. Between the two viewing stations the glass is fully supported across its whole width by the two rollers 10 and at the second viewing station 7 where the previously supported half of the ribbon is now unsupported, the previously unsupported and examined half is now supported while examination of the unsupported ribbon half takes place at the viewing station 7. In this way there is little risk of damage to the ribbon and there is no obstruction to the visual examination of the whole of the width of the ribbon for defects.

For a ribbon speed on the conveyor of 0.25 m/s the examiner at each viewing station has about 7 seconds viewing time for any defect.

Figure 2:
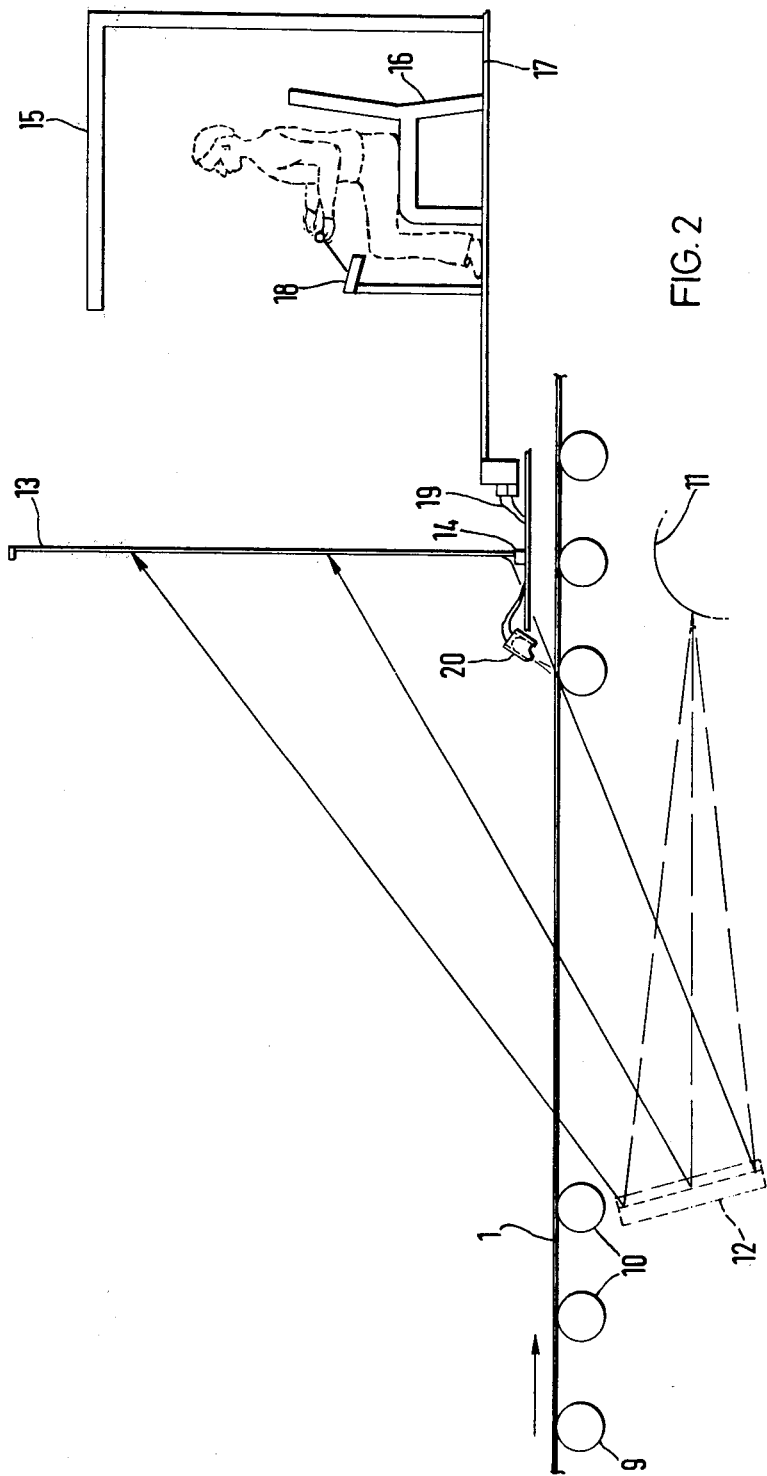
FIG. 2 is an elevation, partly in section on line II—II on FIG. 1.

At the viewing station 6 there is a mercury lamp 11 positioned beneath the conveyor in a position between the two full width rollers 10. A reflector in the form of a concave mirror 12 is also positioned beneath the ribbon and is spaced away from the light source 11 at the upstream end of the viewing area. The mirror 12 has a radius of curvature of 4.2 m and is cut to rectangular shape having overall dimensions of 0.50 m × 1.83 m. The mirror, as shown in FIG. 2 is inclined at an angle of about 15° to the vertical so that it reflects light from the source 11 obliquely upwards through the gap between the conveyor rollers. This light is transmitted obliquely through the flat glass on the conveyor and is incident on a viewing screen 13 which is located in an upright position on a support 14, shown in FIG. 2, above the second of the full width conveyor rollers 10. The mirror 12 is held in a carriage assembly (not shown) beneath the conveyor. The carriage assembly is mounted on a short rail section which allows the mirror 12 to be moved in and out of position, using a small hand winch mechanism. To replace the mirror 12, the carriage assembly is moved approximately one meter in a downstream direction. This motion causes the carriage frame to swing from its normal 15° attitude to assume a horizontal position. The mirror can then be removed from beneath the conveyor by operation of the hand winch mechanism and a new mirror installed on the carriage assembly which is then wound back into position. At the second viewing station 7 for the other half of the glass ribbon there is an identical arrangement of a mercury lamp 11 a mirror 12 and an upright screen 13. The lamp 11 is positioned between the first two full width conveyor rollers following the viewing station 7, the mirror 12 is positioned beneath the second of the two full width conveyor rollers 10 between the two viewing stations and the viewing screen 13 is positioned above the second of the full width conveyor rollers following the viewing station 7.

Each of the viewing screens 13 is a rear-projection screen and an examiner sits in a booth 15 behind the screen as illustrated in FIG. 2. The examiner's chair 16 is on a platform 17 positioned over the conveyor behind both the screens. The platform 17 has a stepped cutaway shape as indicated in FIG. 1. The two examiners are thus located near to each other each viewing his own screen so that each examiner is responsible for locating defects in only half of the width of the ribbon. Each of the rear-projection screens 13 is made of a cellular plastic material and is about 2 m wide by 1.8 m high. In front of each of the examiners there is an operating console 18 which is connected by control lines 19 to a bank of marker guns 20 which are positioned on the support 14 above the conveyor. The marker guns 20 of each bank are spaced apart at regular intervals and when the examiner sees the image of a defect occurring as a shadow on his screen he can mark the glass where that defect occurs by operating, through his console 18, the marker gun nearest to the defect.

When the ribbons have longitudinal score lines the defect may occur on a side of a score line opposite to the side over which the nearest marker gun is located. In such a case it is clearly necessary to operate a marker gun which is nearest to the defect and also on the same side of the score line. To facilitate this operation manually set pointers can be located across the screen, the positions of the pointers representing respectively the score lines on the ribbon. An examiner can determine on which side of a pointer the image of the defect occurs and so operate the nearest marker gun on that side. Each marker gun has an associated resettable counter. The counters can be monitored over a specified period to determine marking distribution across the ribbon and give an indication of the number of defects.

A defect in the half of width of the ribbon being examined by any one of the examiners comes into view as the glass passes into the viewing area at the viewing station. The defect will then be a shadow at the top of the screen 13. This shadow moves downwardly towards the bottom of the screen at a progressively slower speed. The speed decreases as the distance between the image on the screen and the glass surface decreases. A shadow image of the marker guns 20 also appears near the bottom of the screen and when the shadow image of the defect approaches the marker guns the examiner fires the appropriate gun to mark the ribbon. The ink may not fall directly on the defect but it will fall on the same transverse line so that during crosscutting of the ribbon the ink mark and the defect which it is marking are not separated.

The marker guns 20 can be set to be actuated automatically at intervals when a continuous or regularly spaced defect appears on the glass ribbon. A single examiner can keep an eye on both screens when only very gross defects are to be identified and ribbon speeds are low. Generally ribbon examination is a two man operation with the two screens 13 being viewed individually. Four men may be used at higher ribbon speeds and when there is a greater density of faults.

The optical system may include an arrangement for projecting an image of a defect of standard size onto the screen to act as a reference standard for the examiner.

An automatic examination system may be used. For example each human examiner may be replaced by one or more cameras which are mounted to view the viewing screen and to detect the shadow of a defect which moves down the screen. The cameras are connected to an automatic system for operating the marker guns, and the appropriate marker gun is operated automatically in response to the sensing of a shadow of a defect.

The invention thus provides improved apparatus for inspecting flat glass for defects which gives greater certainty of marking of defects on the transverse line of the ribbon width where that defect occurs and leaving at most half of the ribbon width unsupported during examination.

We claim:

1. Apparatus for inspecting flat glass for defects, comprising: a conveyor having a width sufficient to support the glass, two viewing stations disposed one on each side of the centre line of the conveyor and longitudinally displaced relative to each other along the direction of travel of the conveyor, the conveyor extending over only part of the conveyor width at each viewing station to provide an uninterrupted viewing area for viewing slightly more than one half of the glass width at each viewing station, and to provide support for part of the glass alongside each viewing area, a light source and a reflector at each viewing station, the reflector being positioned to reflect light from the source obliquely through said slightly more than one half of the width of the flat glass on the conveyor moving through the viewing area at that viewing station, and a viewing screen positioned to receive the reflected light after its passage through the glass.

2. Apparatus according to claim 1, wherein the conveyor is a roller conveyor and the conveyor rollers extend over only part of the conveyor width at each viewing station to support a part of the glass alongside each viewing area and provide said uninterrupted viewing area at each viewing station.

3. Apparatus according to claim 2, wherein the conveyor rollers end just short of the centre line of the conveyor alongside each viewing station so that each viewing area extends over the centre line of the conveyor to facilitate detection of defects in the part of the glass supported by the central part of the conveyor.

4. Apparatus according to claim 1, claim 2, or claim 3, wherein each viewing screen is located in an upright position above the conveyor, and the light source and reflector at each viewing station are positioned below the conveyor to reflect light obliquely through the glass on the conveyor at an acute angle to the plane of the conveyor, whereby an image of a defect in the glass first appears at the top of the screen and moves down the screen at a progressively slower speed as the defect moves towards the bottom of the screen.

5. Apparatus according to claim 1, claim 2 or claim 3, wherein each viewing screen is a rear-projection screen which is located in an upright position above the conveyor, the light source and reflector at each viewing station are positioned below the conveyor to reflect light obliquely through glass on the conveyor at an acute angle to the plane of the conveyor which light is incident on the front of the screen, and a platform for an examiner is positioned over the conveyor behind the screen so that the examiner can view the rear face of the screen.

6. Apparatus according to claim 1, claim 2 or claim 3, including, at each viewing station, a bank of marker guns positioned above the conveyor, an operating console connected to the marker guns which console is positioned for operation by an examiner viewing the screen to cause the appropriate marker gun to mark the glass in the vicinity of any defect whose image on the screen is recognised by the examiner.

* * * * *